(12) United States Patent
Clarke et al.

(10) Patent No.: US 7,524,671 B2
(45) Date of Patent: *Apr. 28, 2009

(54) HANDHELD RAMAN BLOOD ANALYZER

(75) Inventors: Richard H. Clarke, Big Sky, MT (US); M. Edward Womble, Austin, TX (US)

(73) Assignee: Prescient Medical, Inc., Doylestown, PA (US)

( * ) Notice: Subject to any disclaimer, the term of this patent is extended or adjusted under 35 U.S.C. 154(b) by 161 days.

This patent is subject to a terminal disclaimer.

(21) Appl. No.: 10/905,956

(22) Filed: Jan. 27, 2005

(65) Prior Publication Data

US 2006/0166302 A1 Jul. 27, 2006

(51) Int. Cl.
C12M 1/34 (2006.01)
(52) U.S. Cl. .................................. 435/287.1
(58) Field of Classification Search ................. None
See application file for complete search history.

(56) References Cited

U.S. PATENT DOCUMENTS

| | | |
|---|---|---|
| 3,598,727 A | 8/1971 | Willock |
| 3,900,396 A | 8/1975 | Lamadrid |
| 4,127,033 A | 11/1978 | Warren et al. |
| 4,172,033 A | 10/1979 | Willock |
| 4,267,040 A | 5/1981 | Schal |
| 4,329,986 A | 5/1982 | Babb |
| 4,370,983 A | 2/1983 | Lichtenstein |
| 4,573,761 A | 3/1986 | McLachlan et al. |
| 4,733,253 A | 3/1988 | Daniele |
| 4,769,134 A | 9/1988 | Allan et al. |
| 4,781,458 A | 11/1988 | Angel et al. |
| 4,913,142 A | 4/1990 | Kittrell et al. |
| 5,011,284 A | 4/1991 | Tedesco et al. |
| 5,112,127 A | 5/1992 | Carrabba et al. |
| 5,139,334 A | 8/1992 | Clarke |
| 5,199,431 A | 4/1993 | Kittrell et al. |
| 5,266,498 A | 11/1993 | Tarcha et al. |
| 5,280,788 A | 1/1994 | Janes et al. |
| 5,290,275 A | 3/1994 | Kittrell et al. |
| 5,304,173 A | 4/1994 | Kittrell et al. |
| 5,318,024 A | 6/1994 | Kittrell et al. |
| 5,372,135 A | 12/1994 | Mendelson et al. |
| 5,376,556 A | 12/1994 | Tarcha et al. |
| 5,377,004 A | 12/1994 | Owen et al. |
| 5,381,237 A | 1/1995 | Sela |
| 5,400,136 A | 3/1995 | Vo-Dinh |
| 5,419,323 A | 5/1995 | Kittrell et al. |
| 5,439,000 A | 8/1995 | Gunderson et al. |
| 5,445,972 A | 8/1995 | Tarcha et al. |
| 5,452,723 A | 9/1995 | Wu et al. |
| 5,455,673 A | 10/1995 | Alsmeyer et al. |
| 5,534,997 A | 7/1996 | Schrader |
| 5,553,616 A | 9/1996 | Ham et al. |
| 5,562,100 A | 10/1996 | Kittrell et al. |
| 5,567,628 A | 10/1996 | Tarcha et al. |
| 5,615,673 A | 4/1997 | Berger et al. |
| 5,621,522 A | 4/1997 | Ewing et al. |
| 5,657,404 A | 8/1997 | Buchanan et al. |
| 5,685,988 A | 11/1997 | Malchesky |
| 5,693,043 A | 12/1997 | Kittrell et al. |
| 5,697,373 A | 12/1997 | Richards-Kortum et al. |
| 5,715,263 A | 2/1998 | Ventrudo et al. |
| 5,751,415 A | 5/1998 | Smith et al. |
| 5,773,835 A | 6/1998 | Sinofsky |
| 5,815,260 A | 9/1998 | Dou et al. |
| 5,817,007 A | 10/1998 | Fodgaard et al. |
| 5,842,995 A | 12/1998 | Mahadevan-Jansen et al. |
| 5,849,179 A | 12/1998 | Emerson et al. |
| 5,858,186 A | 1/1999 | Glass |
| 5,862,273 A | 1/1999 | Pelletier |
| 5,864,397 A | 1/1999 | Vo-Dinh |
| 5,870,188 A | 2/1999 | Ozaki et al. |
| 5,902,246 A | 5/1999 | McHenry et al. |
| 5,902,247 A | 5/1999 | Coe et al. |

(Continued)

FOREIGN PATENT DOCUMENTS

DE 4433305 4/1996

(Continued)

OTHER PUBLICATIONS

Bao et al. Anal Chem 2004;76(15)4531-4536.*

(Continued)

*Primary Examiner*—Jon P Weber
*Assistant Examiner*—Bin Shen
(74) *Attorney, Agent, or Firm*—Michele V. Frank; Patton Boggs LLP

(57) ABSTRACT

Methods and apparatus for in vitro detection of an analyte in a blood sample using low resolution Raman spectroscopy are disclosed. The blood analyzer includes a disposable strip for receiving a sample of blood on a target region, the target region including gold sol-gel to provide surface enhanced Raman scattering. A light source irradiates the target region to produce a Raman spectrum consisting of scattered electromagnetic radiation that is separated into different wavelength components by a dispersion element. A detection array detects a least some of the wavelength components of the scattered light and provides data to a processor for processing the data. The results of the processed data are displayed on a screen to inform a user about an analyte within the blood sample.

24 Claims, 4 Drawing Sheets

U.S. PATENT DOCUMENTS

| | | | |
|---|---|---|---|
| 5,951,482 | A | 9/1999 | Winston et al. |
| 5,982,484 | A | 11/1999 | Clarke et al. |
| 5,991,653 | A | 11/1999 | Richards-Kortum et al. |
| 5,993,378 | A | 11/1999 | Lemelson |
| 6,018,389 | A | 1/2000 | Kyle et al. |
| 6,038,887 | A | 3/2000 | Vild et al. |
| 6,044,285 | A | 3/2000 | Chaiken et al. |
| 6,064,897 | A | 5/2000 | Lindberg et al. |
| 6,087,182 | A | 7/2000 | Jeng et al. |
| 6,095,982 | A | 8/2000 | Richards-Kortum et al. |
| 6,144,444 | A | 11/2000 | Haworth et al. |
| 6,151,522 | A | 11/2000 | Alfano et al. |
| 6,154,596 | A | 11/2000 | Ionov |
| 6,156,002 | A | 12/2000 | Polaschegg et al. |
| 6,174,291 | B1 | 1/2001 | McMahon et al. |
| 6,208,887 | B1 | 3/2001 | Clarke |
| 6,212,424 | B1 | 4/2001 | Robinson |
| 6,219,137 | B1 | 4/2001 | Vo-Dinh |
| 6,226,082 | B1 | 5/2001 | Roe |
| 6,258,027 | B1 | 7/2001 | Sternby |
| 6,281,971 | B1 | 8/2001 | Allen et al. |
| 6,284,131 | B1 | 9/2001 | Hogard et al. |
| 6,284,141 | B1 | 9/2001 | Shaldon et al. |
| 6,310,686 | B1 | 10/2001 | Jiang |
| H2002 | H | 11/2001 | McLachlan et al. |
| 6,313,914 | B1 | 11/2001 | Roe |
| 6,373,567 | B1 | 4/2002 | Wise et al. |
| 6,486,948 | B1 | 11/2002 | Zeng |
| 6,507,747 | B1 | 1/2003 | Gowda et al. |
| 6,511,814 | B1 | 1/2003 | Carpenter |
| 6,514,767 | B1 | 2/2003 | Natan |
| 6,560,478 | B1 | 5/2003 | Alfano et al. |
| 6,574,501 | B2 | 6/2003 | Lambert et al. |
| 6,580,935 | B1 | 6/2003 | Wach et al. |
| 6,621,574 | B1 | 9/2003 | Forney et al. |
| 6,643,012 | B2 | 11/2003 | Shen et al. |
| 6,666,840 | B1 | 12/2003 | Falkvall et al. |
| 6,690,966 | B1 | 2/2004 | Rava et al. |
| 6,721,583 | B1 | 4/2004 | Durkin et al. |
| 6,750,065 | B1 | 6/2004 | White et al. |
| 6,750,963 | B2 | 6/2004 | Sampas |
| 6,770,488 | B1 | 8/2004 | Carron et al. |
| 6,841,159 | B2 | 1/2005 | Simonson |
| 6,844,200 | B2 | 1/2005 | Brock |
| 6,897,951 | B2 | 5/2005 | Womble et al. |
| 6,924,153 | B1 | 8/2005 | Boehringer et al. |
| 7,102,746 | B2 | 9/2006 | Zhao |
| 7,245,369 | B2 | 7/2007 | Wang et al. |
| 7,326,576 | B2 | 2/2008 | Womble et al. |
| 7,351,212 | B2 | 4/2008 | Roe |
| 7,374,546 | B2 | 5/2008 | Roe et al. |
| 2003/0105069 | A1 | 6/2003 | Robinson et al. |
| 2003/0231305 | A1 | 12/2003 | Zeng |
| 2004/0116829 | A1 | 6/2004 | Raney et al. |
| 2004/0127789 | A1 | 7/2004 | Roe |
| 2004/0127819 | A1 | 7/2004 | Roe |
| 2004/0160601 | A1 | 8/2004 | Womble et al. |
| 2004/0174520 | A1 | 9/2004 | Premashlri et al. |
| 2004/0186394 | A1 | 9/2004 | Roe et al. |
| 2004/0188394 | A1 | 9/2004 | Roe et al. |
| 2004/0191921 | A1 | 9/2004 | Farquharson et al. |
| 2004/0204634 | A1 | 10/2004 | Womble et al. |
| 2005/0059894 | A1 | 3/2005 | Zeng et al. |
| 2005/0105084 | A1 | 5/2005 | Wang et al. |
| 2005/0128476 | A1 | 6/2005 | Zhao |
| 2005/0171436 | A1 | 8/2005 | Clarke et al. |
| 2005/0250141 | A1 | 11/2005 | Lambert et al. |
| 2005/0264808 | A1 | 12/2005 | Wang |
| 2006/0166302 | A1 | 7/2006 | Clarke et al. |
| 2006/0176476 | A1 | 8/2006 | Clarke et al. |
| 2006/0240401 | A1 | 10/2006 | Clarke et al. |
| 2007/0059203 | A1 | 3/2007 | Burrell et al. |
| 2007/0224683 | A1 | 9/2007 | Clarke et al. |
| 2008/0064120 | A1 | 3/2008 | Clarke et al. |

FOREIGN PATENT DOCUMENTS

| | | |
|---|---|---|
| EP | 1646571 | 10/2007 |
| JP | 2007/553245 | 7/2007 |
| WO | WO 99/10742 | 3/1999 |
| WO | WO 2006/061380 | 8/2006 |
| WO | WO 2007/089540 | 8/2007 |
| WO | WO 2007/089551 | 8/2007 |
| WO | WO 2007/092173 | 8/2007 |

OTHER PUBLICATIONS

Goodridge "Rapid on-site cyanide assay for blood and saliva samples", Database: Toxcenter, DN Crisp-2003-GM68246-01, 2004, Abstract.*

Hanlon E.B. et al. "Prospects for in vivo Raman spectroscopy," Phys. Med. Biol. 45 (2000) R1-R59.

Premasiri, W. Ranjith et al. "Urine Analysis by Laser Raman Spectroscopy," Lasers in Surgery and Medicine 28 (2001) pp. 330-334.

Clarke, R. H. et al. "Low-resolution Raman Spectroscopy as an Analytical Tool for Organic Liquids," Spectroscopy 13 (Oct. 1998) pp. 28-35 (downloaded on Jul. 31, 2003 from www.oceanoptics.com. products/ramanarticle.asp).

Clarke R. H. et al. "Low-Resolution Raman Spectroscopy: Instrumentation and Applications in Chemical Analysis," Journal of Raman Spectroscopy 30 (1999) pp. 827-832.

Berger, Andrew J. et al. "MUlticomponent blood analysis by near-infrared Raman spectroscopy," Applied Optics 38:13 (May 1, 1999) pp. 2916-2926.

Berger, Andrew Joshua. "Measurement of analytes in human serum and whole blood samples by near-infrfed Raman spectroscopy," Ph.D. Dissertation, Massachusetts Institute of Technology, Jun. 1998.

"RamanProbe" brochure published by InPhotonics no publication date available.

Womble, M. Edward et al. "Low-Resolution Raman Method Offers Low Cost and Portability," Laser Focus World (Apr. 1999) pp. 131-136.

International Search Report dated Sep. 11, 2007 for corresponding International Application No. PCT/US07/02062.

Bao et al.; Anal Chem 2004; 76(15) 4531-4536.

U.S. Appl. No. 11/698,083, filed Jan. 26, 2007, Clarke et al.

"RamanProbe" brochure published by InPhotonics no publication date available, 1999.

Berger, A. J. et al., "Rapid, noninvasive concentration measurements of aqueous biological analytes by near-infrared Raman spectroscopy," Applied Optics, 1996, 35(1):209-212.

Berger, A. J. et al., "Feasibility of measuring blood glucose consentration by near-infrared Raman spectroscopy," Spectrochimica Acta Part A, 1997; 53:287-292.

Brennan, J. F. et al., "Histochemical Analysis of Human Coronary Artery Using Near-Infrared Raman Spectroscopy," Proc. Of SPIE; 1995; 2324:98-102.

Kneipp, K. et al., "Near-infrared surface-enhanced Raman scattering (NIR-SERS) of neurotransmitters in colloidal silver solutions," Spectrochimica Acta, 1995; 51(A)(3):481-487.

Liistro, F. et al., "First Clinical Experience With a Paclitaxel Derivate-Eluting Polymer Stent System Implantation for In-Stent Restenosis: Immediate and Long-Term Clinical and Angiographic Outcome," Circulation, 2002; 105, 1883-1886.

Morice, M. et al., "A Randomized Comparison of a Sirolimus-Eluting Stent with a Standard Stent for Coronary Revascularization," N. Engl. J. Med., 2002; 346(23):1773-1780.

Sharma, S. et al., Correction "Sirolimus-Eluting Coronary Stents," N. Engl. J. Med., 2002; 347:1285.

Nave, S.E., "Rugged Fiber Optic Probes and Sampling Systems for Remote Chemical Analysis Via the Raman Technique," Advances in Instrumentation and Control, 1996; 51:453-467.

Qu. J. Y. et al, "Rapid quantification of the clinically important analytes in sub-μl simulating human sera," Proc. of SPIE, 2000, 3918:174-180.

Römer, T. J. et al., "Histopathology of Human Coronary Atherosclerosis by Quantifying Its Chemical Composition with Raman Spectroscopy," Cirulation 1998; 97:878-885.

Schultz, C. P. et al, "A Comparison of Non-destructive and Non-invasive material depth profiling using FT-Raman fiber optics and microspectroscopy," Proc. Of SPIE, 2000; 4129:284-293.

Serruys, P.W. et al., "Intravascular Ultrasound Findings in the Multicenter, Randomized, Double-Blind RAVEL (Randomized study with the sirolimus-eluting Velocity balloon-expandable stent in the treatment of patients with de novo native coronary artery Lesions) Trial," Circulation, 2002, 106:798-803.

Shim, M.G. et al, "Evaluation of fiber optic probes for in vivo Raman spectroscopy," SPIE, 1998; 3257:208-217.

Walker, P.A. III et al., "Capillary isotachophoresis with fiber-optic Raman spectroscopic detection Performand and application to ribonucleotides," Journal of Chromatography A, 1998; 805:269-275.

Williams, K.P.J., "Remote Sampling Using a Fibre-Optic Probe in Fourier Transform Raman Spectroscopy," Journal of Raman Spectroscopy, 1990; 21: 147-151.

Zimba, C.G. et al., "FT-Raman Spectroscopy with Fiber-Optic Probes and a Diode-Bar-Pumped Nd:YAG Laser," Applied Spectroscopy, 1991; 45: 162-165.

International Search Report, PCT/US2007/002106, dated Apr. 7, 2008.

International Search Report, PCT/US2007/002108, dated Nov. 20, 2007.

* cited by examiner

HANDHELD RAMAN BLOOD ANALYZER

BACKGROUND OF THE INVENTION

The present invention generally relates to methods and apparatus for testing biological samples, and in particular, to systems for in vitro testing of blood samples for analytes, such as metabolic products, drugs or toxins.

The ability to monitor an analyte within a blood sample has greatly improved the diagnosis and treatment of diseases. For example, home monitors allow diabetics to test glucose levels by pricking their finger and applying a small sample of blood to a test strip. Based on the glucose reading, diet and/or insulin dosage can be adjusted.

Generally, these in vitro glucose monitor systems use an electrochemical detection technique based on glucose oxidase reactions. The system can include a disposable strip having electrodes and the glucose oxidase enzyme. When a blood drop is applied to the target area of the electrode, the glucose oxidase catalyzes the oxidation of glucose in the drop to produce gluconic acid. During the reaction, electrons are transferred by an electrochemical mediator to the electrode surface. This in turn generates a current that is measured by the sensor. The amount of current generated is proportional to the amount of glucose present in the blood drop, thus giving an accurate reading of the blood glucose concentration.

While the ease of use and the low cost of these home monitor systems have proven helpful for regular blood sugar monitoring, they are limited by the amount of information that can be provided using a glucose oxidase reaction. Information on other substances within the blood is not readily available without incorporation of additional reagents and assays.

For these reasons, there continues to exist a need in this art for better devices and methods for testing blood samples.

BRIEF SUMMARY OF THE INVENTION

The present invention provides methods and apparatus for in vitro detection of analytes in a blood sample using low resolution Raman spectroscopy. The apparatus preferably employs a multimode laser source for radiating a sample and producing a Raman spectrum consisting of scattered electromagnetic radiation. The radiation is then separated into different wavelength components by a low resolution dispersion element and detected by a detection array. Data from the array is processed by a processor to provide information about one or more analytes.

In one aspect of the invention, the handheld Raman analyzer can provide information about multiple analytes. For example, the analytes can include blood components and/or metabolic products such as insulin, hemoglobin, cholesterol, electrolytes, antioxidants, nutrients, or blood gases. Other analytes that can be detected and/or monitored with the present invention include prescription or illicit drugs, alcohol, poisons, and disease markers.

In another aspect, a system is disclosed including a disposable test strip that provides surface enhanced Raman Scattering (SERS). In one embodiment, the test strip can include a metallic surface or a surface that includes metallic (e.g., silver or gold) particles. One preferred embodiment is a test strip with a sample-receiving region that includes gold nanoparticles stabilized in a porous sol-gel silicate. The sol-gel can be deposited as a layer over at least a portion of the strip or it can be a discrete application of material, e.g., printed as a dot, which defines the sample-receiving region for analysis.

In another aspect, the present invention includes a method for analyzing blood samples including providing a disposable strip for receiving a sample of blood on a target region and depositing the sample of blood on the target region of the disposable strip. The target area is then irradiated with a laser to produce a Raman spectrum consisting of scattered electromagnetic radiation which is separated into different wavelength components using a low resolution dispersion element. At least some of the wavelength components are detected using a detection array and the resulting data is processed by a processor to asses an analyte within the blood sample. Results from the processor may optionally be displayed on a screen.

BRIEF DESCRIPTION OF THE DRAWINGS

The invention will be more fully understood from the following detailed description taken in conjunction with the accompanying drawings.

DETAILED DESCRIPTION OF THE INVENTION

The present invention generally relates to a system for in vitro detection of one or more analytes in a blood sample using low resolution Raman spectroscopy. The system preferably includes a disposable strip for receiving a sample of blood on a target region (e.g., a small spot of sol-gel material on the strip) and a laser for irradiating the target region to produce a Raman spectrum consisting of scattered electromagnetic radiation. A low resolution dispersion element, positioned to receive the scattered radiation, preferably separates the radiation into different wavelength components, and at least some of the wavelength components are then detected by a detection array. Data from the detection array is passed to a processor for processing the data and for testing an analyte within the blood sample. The system can also evaluate multiple analytes within the blood sample.

While conventional blood glucose monitors have improved home monitoring of blood glucose levels, such electrochemical devices fail to inform the user about other important substances within the blood. Testing of other analytes can be performed in medical laboratories, but at significant time and expense. The present invention overcomes these drawbacks by using low resolution Raman spectroscopy, in a handheld device, to detect analytes within a blood sample. The handheld device of the present invention provides a cost efficient method for testing multiple analytes in a single sample.

Figure 1:
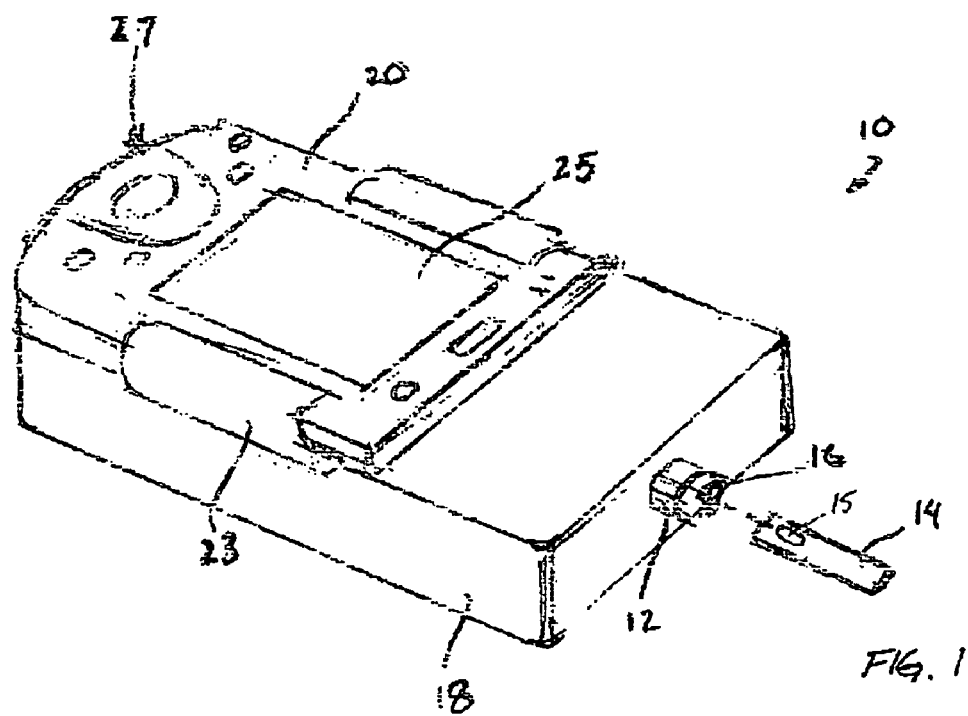
FIG. 1 is a schematic, perspective illustration of one embodiment of a handheld Raman blood analyzer according to the present invention.

FIG. 1 illustrates one embodiment of a handheld Raman analysis device 10 according to the present invention including a sampling port 12 for receiving a test strip 14 within a target area 16. The test strip includes an analysis site 15 on which a blood sample or similar analyte has been deposited. Spectroscopic components, positioned within device 10 and described below, produce radiation and provide spectroscopic measurements of the sample. Results from the spectroscopic analysis can be communicated directly to an attached PC device 20 as shown, having a screen 25 and user interface/controls 27. The pocket PC (or similar PDA type device) can be coupled to the analyzer 10 by guide rails 22 and conventional electronic connectors. Alternatively, the results of the spectroscopic analysis can be communicated via a wireless transmitter or hardwired connection to a suitable data processor.

Figure 2:
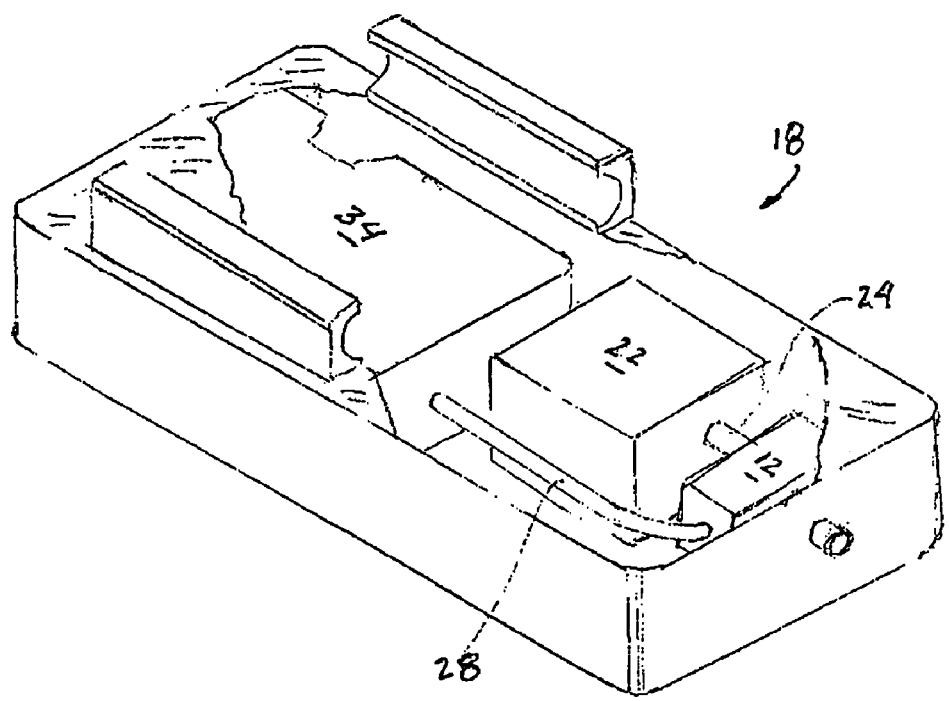
FIG. 2 is a schematic illustration of the analytical components of the device of FIG. 1.

A more detailed view of spectroscopic components 18 is provided in FIG. 2, including a multi-mode laser source 22 and optical fiber 24 connected to the laser source for carrying laser light to the sampling port 12. Relay optics can optionally be used with the optical fiber to focus and direct the radiation. A person skilled in the art will appreciate that optical fiber 24 may includes the variety of optical fibers and light carrying materials that can collect and direct radiation.

Light is preferably directed by optical fiber 24 to the sampling area 12, and after encountering the blood sample, Raman scattered light is routed by a second optical fiber 28 to a spectroscopic analyzer 34.

Figure 3:
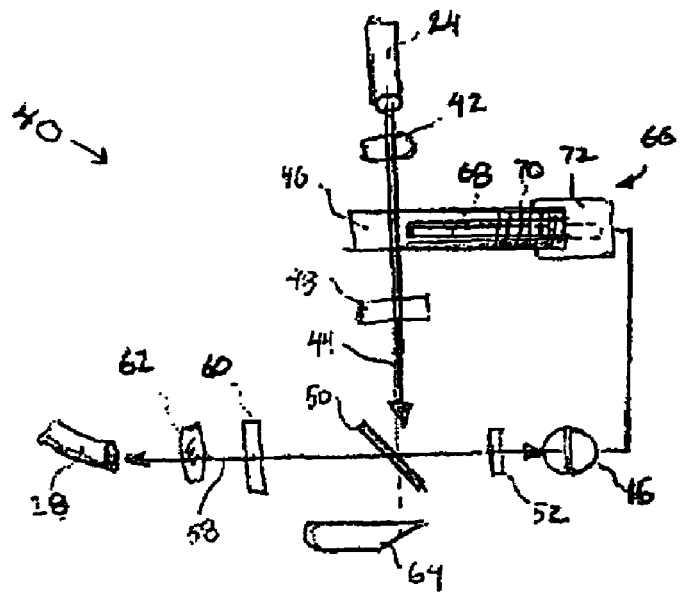
FIG. 3 is a schematic illustration of the sampling components of the device of FIG. 1.

In one embodiment, the sampling port 12 includes an optical assembly 40 as illustrated schematically in FIG. 3. Optical assembly 40 directs the light received from light source 22 into position for contacting the sample, collects the scattered radiation, and returns the collected radiation for analysis.

Excitation radiation enters optical assembly 40 via optical fiber 24. The beam from the input fiber is passed through lens 42, which serves to collimate or otherwise project the incoming radiation along beam path 44 with minimal dispersion. The radiation from lens 42 then passes through an optional safety switch 66 including chamber 46 and through one or more optional filters 48, e.g., a low-pass filter.

The filtered incoming light is then reflected by dichroic beam-splitter 50 (which is designed to reflect nearly all of the excitation light) and directed toward target area 16. A second lens 52 can be disposed to focus the excitation radiation to a particular point or region within a sample 54. Preferably, lens 52 focuses the light on target area 16.

Returning radiation 56 passes through lens 52, which now serves to collimate the scattered radiation and convey it to collection fiber 28. From lens 52, the collected radiation travels along beam path 58, passing through dichroic beam-splitter 50 and, optionally, a mid-pass or long-pass filter 60 and lens 62. Lens 62 serves to focus the collected radiation into output fiber 28. (It should be appreciated that the lens elements of the present invention can be simple or compound lens assemblies and that the functions that these optical elements perform—directing excitation radiation into a sample and collecting scattered radiation for analysis—can be achieved by various equivalent structures well known to those skilled in the art.)

Optical assembly 40 can further include a "beam dump" 64 to capture and absorb incoming radiation that is not reflected by dichroic beam-splitter 50. Beam dump 64 can comprise a chamber that has been coated with suitable radiation absorbing material or otherwise formed or shaped to ensure that the radiation that is not directed into the sampling tube is captured and dissipated as heat.

Safety switch 66 is formed by a protective shutter, as shown in FIG. 3, that is disposed in chamber 46. Chamber 46 intersects incoming beam path 44. Plunger 68 is disposed within chamber 46 and operatively connected to spring 70 and solenoid 72. In an activated state, solenoid 72, pulls plunger 68 out of light beam path 44, thereby allowing the multimode radiation to pass through optical assembly 40 and to sample 54. In a deactivated state, ("laser blocking" position), the solenoid releases plunger 68, which moves into light beam path 44 and prevents the multimode radiation from passing to the outside environment. Thus, safety switch 66 ensures that the analyzer remains in a "normally-off" state should a malfunction or power loss occur. In one preferred embodiment, the safety switch is connected to a contact sensor in the sampling port that triggers operation only when a test strip is properly inserted into the target area.

Figure 4:
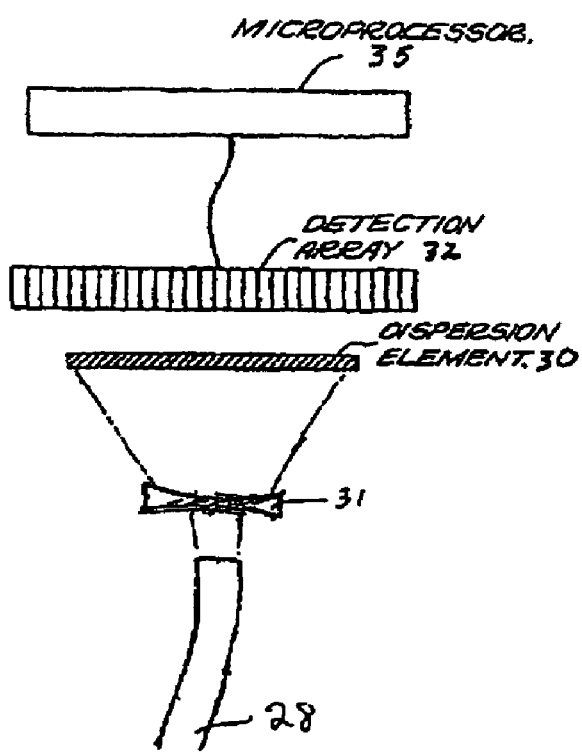
FIG. 4 is a schematic illustration of one embodiment of a Raman spectral analyzer for use in the present invention.

FIG. 4 shows further details of an illustrative spectroscopic analyzer 34 for use in the present invention. Radiation collected from the sampling port 12 by collection fiber 28 is directed through lens 31 and/or dispersion element 30 that serve to disperse the scattered light into different wavelength components. The dispersed scattered light is detected by photodetector array 32 that, in this case, consists of a photodiode array or a charged-coupled device (CCD) array. The signals generated by detector array 32 in response to the scattered light are then sent to a microprocessor 35 for analysis.

The present invention allows specific spectral bands of interest to be measured at low resolution to obtain the integrated band intensities. These bands can be narrow ones. The resolving power of the dispersion device 30 determines the position of specific wavelengths in the diode array in such a way that the signal from a particular diode in the array will typically correspond to the same (or a similar) narrow range of wavelengths. This combination of the low-resolution dispersion device 30 and the diode array photodetector 32 thus form a spectrometer. The microprocessor 34 selects a particular diode (or diodes) of the array 32 according to the property to be measured. The integrated signals lying in the two ranges can be arithmetically divided to form intensity ratios. The microprocessor 34 compares these ratios with known values or a correlating function to obtain an estimate of the chemical constituent or property of interest. In addition, the microprocessor can analyze multiple analytes within a single sample in a single test. In one embodiment, the procedure is repeated for a second analyte by choosing the appropriate diode(s) for the additional analyte. The processor can also run these calculations in series using stored information from the diodes.

The terms "radiation," "laser" and "light" are herein utilized interchangeably. In particular, the term "light" can refer to radiation having wavelength components that lie in the visible range of the electromagnetic spectrum, or outside the visible range, e.g., the infrared or ultraviolet range of the electromagnetic spectrum. In certain embodiments of Raman spectroscopy, the preferred excitation wavelengths will range from about 700 nanometers to 2.5 micrometers. Although this portion of the electromagnetic spectrum is commonly known as infrared (IR) radiation, the term "light" will be used as a shorthand expression in describing the path of this radiation as well as the various wavelengths of radiation induced by Raman scattering and collected for analysis.

Advances in the field of solid-state lasers have introduced several important laser sources into Raman analysis. For high-resolution Raman systems the laser linewidth must be severely controlled, often adding to the cost of the excitation source and the system as a whole. For low resolution Raman spectroscopy (LRRS), however, the strategy of relinquishing resolution details in favor of emphasizing essential identifying spectral features, allows the use of a low cost, high energy multi-mode laser and a low resolution dispersion element. A multi-mode laser which can be used with a LRRS system, according to one embodiment of the present invention, is available in higher power ranges (between 50 mw and 1000 mw) than is available with a traditional single mode laser (<150 milliwatts). The higher power of a multi-mode laser increases the amount of scattered radiation available to the spectrometer system and the sensitivity of the LRRS system increases at least linearly with laser power.

A low resolution dispersion element can provide greater transmission of scattered radiation to the detector array. For example, a low resolution diffraction grating with wider slits than a typical diffraction grating can be used, providing greater transmission of incident scattered radiation to the detector array. Thus, the combination of a low cost, high energy multi-mode laser and a low loss dispersion element provides an inexpensive LRRS system with a high intensity signal.

In a typical LRRS application the need for feature separation is much like that encountered in mid-IR spectroscopy. The use of multi-mode lasers causes degradation in the resolution of the spectrometer. The resolution of the LRRS system decreases primarily because the width of the laser line used to excite the sample is much larger with multi-mode lasers than it is with a single mode laser. A multi-mode laser emits a number of lines on the order of about 1 nanometer within a broader envelope. The envelope can span 2-3 nanometers or more. In comparison, a single mode laser has a linewidth of a fraction of a nanometer. However, one rarely requires single wavenumber resolution to find a spectral fingerprint feature that allows identification and quantification of a sample under analysis. Similarly, in LRRS, since the approach uses fundamental frequencies, even if not fully resolved, in the spectral analysis, a broader band laser source may suffice for the Raman analysis. In this case inexpensive, multi-mode solid-state laser sources are both sufficient for the task and provide cost effective high power.

Since a Raman measurement is the difference in wavelength between the scattered light and the excitation line, an excitation line that has a larger spectral FWHM causes a proportional loss of resolution in the resulting Raman measurement. However, this reduction of resolution is offset by the advantages of lower cost and increased signal intensity. The increased signal intensity is a result of a higher energy laser source and wider slits in the diffraction grating allowing more light into the detector array. Since the spectrometer system resolution has been substantially reduced by the use of a multi-mode laser, the width of the slits can be increased with negligible effect on resolution. In addition, a CCD detector array can be matched to the lower resolution laser source and the dispersion element by reducing the number of elements in the array. For example, instead of 4096 array elements, one can use 2048 larger elements.

Thus, a complete LRRS spectroscopic system can consist of an inexpensive multi-mode laser diode operating at a higher power (between 50 mw and 1000 mw output) than traditional single-mode Raman sources and a low resolution monochromator matched to a simple CCD detector, with Rayleigh filtering provided by edge or notch filters capable of removing the excitation source background.

Resolution of the low-resolution Raman spectroscopy is preferably between 10 $cm^{-1}$ and 100 $cm^{-1}$ and most preferably between 30 $cm^{-1}$ and 50 $cm^{-1}$.

Various multi-mode lasers components can be used with the device of the present invention. For example, the B&W Tek multi-mode laser BWF-OEM-785-0.5, available from B&W Tek, Inc., of Newark, Del., can be used as the multi-mode laser. Alternatively, the multi-mode laser can be a custom built. The optical fibers utilized in the present invention apparatus of the invention are preferably multimode fibers, which are available from several commercial sources including, for example, Fiberguide, Inc. of Sterling, N.J. Their diameters may range from 1 µm to 1000 µm, preferably from about 100 µm to about 400 µm, and more preferably from about 100 µm to about 200 µm. Single fibers and fiber bundles can also be utilized in the present invention. In addition, various low resolution monochromators can be used as detector arrays. For example, Ocean Optics S-1000 and S-2000 monochromators are commercially available from Ocean Optics of Dunedin, Fla. Optical filters can be used to eliminate the Rayleigh line.

The microprocessor used with the device of the present invention can include any computer with sufficient storage capacity and processing capability to house a library of blood components for matching and quantifying. An exemplary microprocessor is the Compaq iPAQ from the Hewlett-Packard Company.

The handheld Raman device of the present invention can additionally include a disposable test strip 14. Test strip 14, pictured in FIG. 1, preferably provides an area to deposit a blood sample onto which the laser radiation is directed, and even more preferably, includes features to enhance spectroscopy. In one embodiment, the test strip can include a substance for surface enhanced Raman spectroscopy (SERS).

Figure 5:
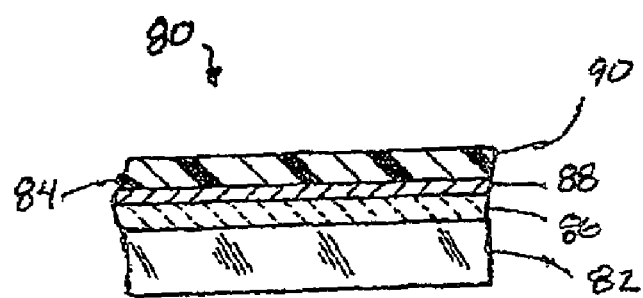
FIG. 5 is a schematic illustration of test strip including a surface enhanced Raman spectrometry material for use in the present invention.

SERS techniques enhance Raman spectroscopic signals and allow more effective differentiation of spectroscopic signatures by placing the sample to be analyzed in contact with SERS material (usually an appropriately prepared metal surface). Two mechanisms are considered responsible for the improvement. The primary contribution is an enlargement of the local electromagnetic field, due to the excitation of a localized surface plasmon, while the other mechanism results from a charge transfer-state between the surface complex of the adsorbed molecule and the metal surface Preferably, a SERS test strip includes SERS-active material, such as, for example silver, gold, nickel, copper and/or cadmium. FIG. 5 illustrates one exemplary embodiment of SERS active test strip 80 including a support substrate 82 and a roughened metal surface layer 84 having a degree of roughness sufficient to induce the SERS effect. Layer 84 may include a microparticle or microstructure layer 86 on the upper surface of support substrate 82 and a metal layer 88 containing silver, gold, nickel, copper, and/or cadmium.

In one embodiment, a porous coating 90 can be applied to roughened surface layer 84 to capture analytes which are not easily deposited on the roughened surface. Coating 90 thus holds analytes which are capable of either penetrating into the coating or being attached to the coating. The analytes are thereby "adsorbed" and become positioned in the vicinity of the roughened surface and exhibit the SERS effect.

In one embodiment, the SERS active material forms the analysis site 15 of the test strip, as shown in FIG. 1. In use, a sample is deposited on the SERS active material in the target area and light is directed toward the sample for spectroscopic analysis. A person of skill in the art will appreciate that the choice of SERS-active material will depend on the desired analyte and the chosen radiation spectrum. In a preferred embodiment, the SERS-active materials include a porous sol-gel containing gold microcollooid particles where the laser radiation is about 785 nm. SERS techniques and materials are described in U.S. Pat. Nos. 5,400,136 and 5,864,397 to Vo-Dinh, which are incorporated herein by reference in their entirety.

In one embodiment, the device of the present invention additionally includes a lancet, which can puncture a user's skin, typically on the user's finger, to draw a blood sample.

The lancet preferably includes a sharpened tip and a mechanism for propelling the metal tip into a user's skin. An exemplary lancet is the BD Ultra-Fine™ Lancet available from BD Consumer Healthcare, Ontario, Canada.

Where the device of the present invention investigates multiple analytes within a single sample during a single analysis it may be particularly advantageous to test analytes related to a single condition. For example, when a patient arrives for a check-up, instead of running two blood tests related to one condition, e.g., one for blood sugar, one for hemoglobin A1c, the present invention allows simultaneous testing. The result is a cost effective and almost immediate analysis.

Other groups of analytes can include a blood chemistry profile (a test for levels of two or more of: urea, creatinine, uric acid, bilirubin, phosphorous, alkaline P-Tase, total protein, albumin, globulin, glucose, calcium, calcium ionized, magnesium, iron, sodium, potassium, chloride, carbon dioxide, T-3 uptake, T-4 RIA, free thyroxine index, TSH-ultra sensitive cholesterol, triglycerides, HDL, LDL, VLDL, iron, iron saturation, and ferritin).

In another embodiment, a mineral and heavy metal assessments may be desirable to reveal the levels of beneficial elements and toxic elements that commonly occur in humans as the result of lifestyle and toxic exposures. Preferred analytes include mercury, iron, calcium, phosphorous, magnesium, and lead. Such a test may be desirable for persons concerned with health hazards in their living or work space.

In yet another embodiment, analytes may be chosen which focus on a certain health condition. For example, testing for analytes related to cardiac health may be desirable during a regular check-up or as part of a heart health screening. Such analytes may include two or more of cholesterol (total, LDL, HDL), triglycerides, c-reactive protein, and homocysteine.

In an additional embodiment, it may be desirable to screen for a group of drugs, and in particular illegal drugs. As an example, analytes could include two or more of marijuana, amphetamines, barbituates, methamphetamines, morphine, heroin, and PCP.

The present invention provides the ability to monitor a variety of analytes using a test simple enough for use at home and sophisticated enough to provide valuable information about select analytes.

The results determined by the processor can be displayed on screen 20. Depending on the particulars of the analyte and the user's needs, the displayed results can be provided in a variety of forms. For example, where glucose is tested, the results can be displayed quantitively (120 mg/dl) or relatively (Normal). With other analytes, it may be desirable to display results indicating only the presence (or absence) of an analyte (e.g., the presence of poisons).

Figure 6:
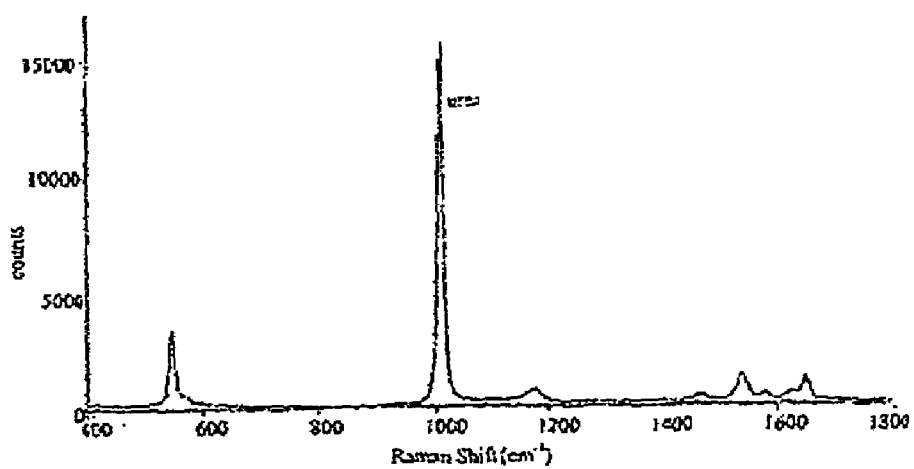
FIG. 6 is a graph of the Raman spectrum of urea.

FIG. 6 is a graph showing the spectrum of pure urea obtained from low resolution Raman spectroscopy. The peak near 1000 cm$^{-1}$ is clearly a pronounced spectral feature and, in accordance with the present invention, can be used for urea identification and analysis. This band corresponds to the symmetrical CN stretch and is the main observable peak at clinical concentration levels.

To investigate the ability to detect urea levels against a more chemically challenging background of blood, Raman spectra of urea in blood plasma were obtained. A series of Raman spectra were run on a commercially obtained (Sigma Chemical) human blood plasma sample to which increasing amounts of urea were added. Resulting spectra show that despite the presence of a nearby interfering peak (at 1000 cm$-1$, due to the aromatic-containing protein phenylalanine), the urea spectrum was evident in the blood plasma sample and fully identifiable in the low resolution regime. These results are graphically illustrated in FIG. 7, which shows how a linear correlation between the peak height at 1001 cm$^{-1}$ and urea concentration.

Figure 7:
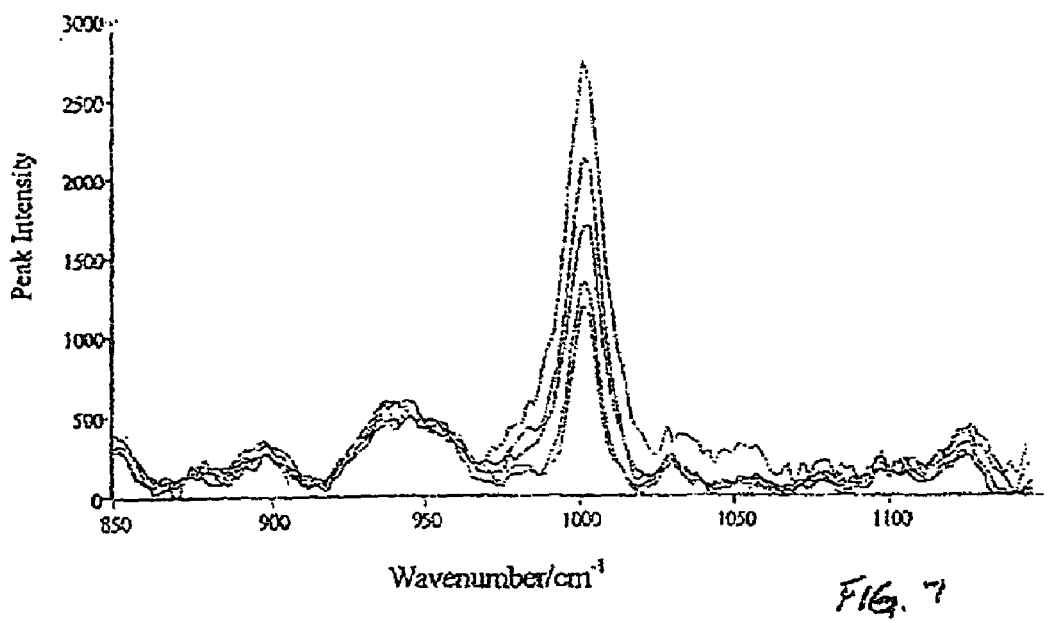
FIG. 7 is a graph showing Raman spectra for blood samples having varying concentrations of urea.
Figure 8:
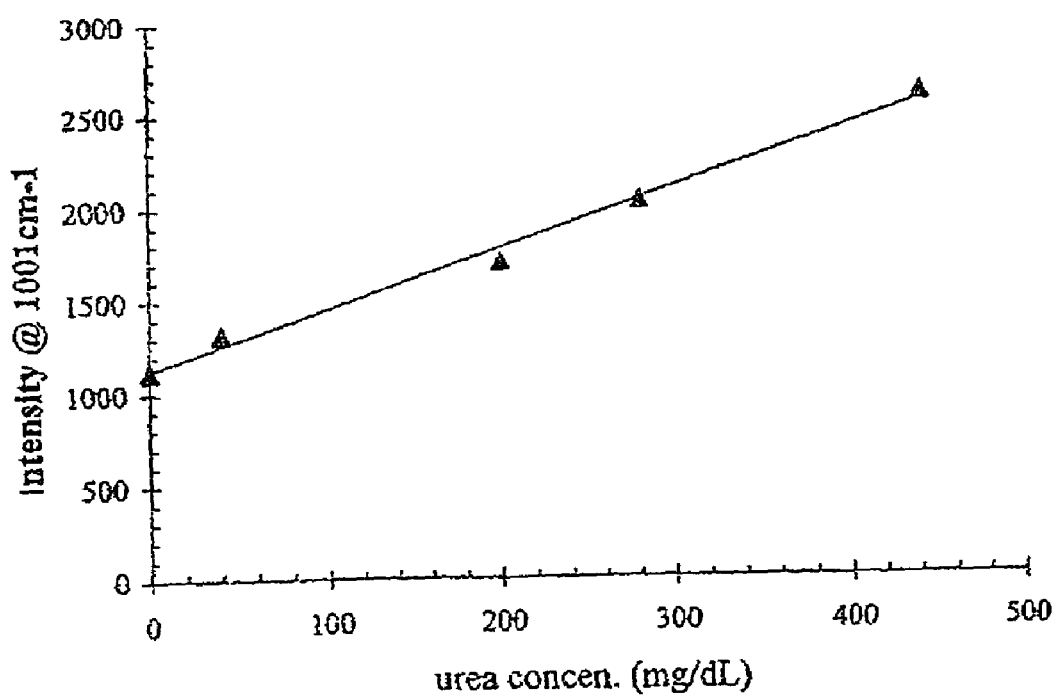
FIG. 8 is graph of the measured intensity of scattered radiation (at 1001 $cm^{-1}$) versus urea concentration for the spectra shown in FIG. 7.

FIG. 8 is graph of the measured intensity of scattered radiation (at 1001 cm$^{-1}$) versus urea concentration for the spectra shown in FIG. 7. The latter result demonstrates the ability of Raman to produce a concentration correlation, since a linear response is the most basic of analytical statistical tools available for extracting urea concentration from the Raman spectral features.

General background information on Raman spectral analysis can be found in U.S. Pat. Nos. 5,139,334, and 5,982,482 issued to Clarke et al. and incorporated herein by reference, which teache low resolution Raman analysis systems for determining certain properties related to hydrocarbon content of fluids. The system utilizes a Raman spectroscopic measurement of the hydrocarbon bands and relates specific band patterns to the property of interest. See also, U.S. Pat. No. 6,208,887 also issued to Clarke and incorporated herein by reference, which teaches a low-resolution Raman spectral analysis system for determining properties related to in vivo detection of samples based on a change in the Raman scattered radiation produced in the presence or absence of a lesion in a lumen of a subject. Additionally, commonly owned, pending U.S. application Ser. No. 10/367,238 entitled "Probe Assemblies for Raman Spectroscopy" and U.S. application Ser. No. 10/410,051 entitled "Raman Spectroscopic Monitoring of Hemodialysis" further describe devices for analyzing samples with Raman spectroscopy. All references cited herein are incorporated by reference in their entirety.

One skilled in the art will appreciate further features and advantages of the invention based on the illustrated embodiments. Accordingly, the invention is not limited by what has been explictly shown and described, except as indicated by the claims. All publications and references cited herein are expressly incorporated herein by reference in their entirety.

What is claimed as new and desired to be protected by Letters Patent of the United States is:

1. An apparatus for in vitro detection of an analyte in a blood sample using low resolution Raman spectroscopy comprising:

a port sized and configured for receiving a test strip comprising a sample of blood on a target region of the test strip;

a light source for irradiating the target region to produce a Raman spectrum consisting of scattered electromagnetic radiation;

a low resolution diffraction grating dispersion element positioned to receive and separate the scattered radiation into different wavelength components;

a detection array, optically aligned with the dispersion element for detecting at least some of the wavelength components of the scattered light; and a processor for processing data from the detector array and calculating information about an analyte within the blood sample, wherein the low resolution diffraction grating dispersion element provides the apparatus with a resolution in the range of 10 cm$^{-1}$ to 100 cm$^{-1}$.

2. The apparatus of claim 1, wherein the processor calculates information about multiple analytes within the blood sample.

3. The apparatus of claim 2, wherein the multiple analytes further comprise at least one blood component.

4. The apparatus of claim 2, wherein the multiple analytes further comprise at least one drug.

5. The apparatus of claim 2, wherein the multiple analytes further comprise at least one disease marker.

6. The apparatus of claim 2, wherein the multiple analytes further comprise at least one poison.

7. The apparatus of claim 1, wherein the concentration of the analyte within the blood sample is calculated.

8. The apparatus of claim 1, wherein the apparatus further comprises the test strip for delivery of the sample and wherein the test strip is disposable.

9. The apparatus of claim 8, wherein the disposable strip further comprises a gold sol-gel strip to provide surface enhanced Raman scattering.

10. The apparatus of claim 1, wherein the light source is a multi-mode laser.

11. The apparatus of claim 1, wherein the processor includes a library of spectral properties of analytes for comparing with spectral information obtained from the blood sample.

12. The apparatus of claim 1, including a screen for displaying information related to the analyte detected within the blood sample.

13. The apparatus of claim 1, wherein the analyte is selected from the group consisting of urea-based compounds, ammonium-based compounds, uric acid based compounds, nitrogen-based compounds, and combinations thereof.

14. The apparatus of claim 1, wherein the detected analyte in the blood sample is selected from the group consisting of cardiac enzymes, cardiovascular stent coatings, poisons, prescription drugs, illicit drugs, hormones, steroids, and combinations thereof.

15. The apparatus of claim 1, including a lancet to puncture a patient's skin.

16. An apparatus for in vitro detection of an analyte in a blood sample using low resolution Raman spectroscopy comprising:
   a strip for receiving a sample of blood on a target region, the target region including a material to provide surface enhanced Raman scattering;
   a laser for irradiating the target region to produce a Raman spectrum consisting of scattered electromagnetic radiation;
   a low resolution diffraction grating dispersion element positioned to receive and separate the scattered radiation into different wavelength components;
   a detection array, optically aligned with the dispersion element for detecting at least some of the wavelength components of the scattered light; and
   a processor for processing data from the detector array and calculating glucose concentration and information about at least one other analyte within the blood sample,
   wherein the low resolution diffraction grating dispersion element provides the apparatus with a resolution in the range of 10 $cm^{-1}$ to 100 $cm^{-1}$.

17. The apparatus of claim 1, wherein the analyte is hemoglobin A1c.

18. The apparatus of claim 11, further comprising the test strip, wherein the target region of the test strip includes gold.

19. The apparatus of claim 11, further comprising the test strip wherein the target region of the test strip includes a sol-gel.

20. A method for in vitro detection of an analyte in a blood sample using low resolution Raman spectroscopy comprising:
   providing a disposable strip for receiving a sample of blood on a target region; depositing a sample of blood on the target region of the disposable strip;
   irradiating the target region with a laser to produce a Raman spectrum consisting of scattered electromagnetic radiation;
   receiving and separating the scattered radiation into different wavelength components using a low resolution diffraction grating dispersion element providing a resolution in the range of 10 $cm^{-1}$ to 100 $cm^{-1}$;
   detecting at least some of the wavelength components of the scattered light using a detection array;
   processing data from the detector array and calculating information about an analyte within the blood sample with a processor; and
   displaying information related to the analyte detected within the blood sample on a screen.

21. The apparatus of claim 1, wherein the port is sized and configured for insertion of the test strip in a longitudinal direction with respect to the longitudinal axis of the test strip.

22. The apparatus of claim 1, wherein the resolution is in the range of 30 $cm^{-1}$ to 50 $cm^{-1}$.

23. The apparatus of claim 16, wherein the resolution is in the range of 30 $cm^{-1}$ to 50 $cm^{-1}$.

24. The method of claim 20, wherein the resolution is in the range of 30 $cm^{-1}$ to 50 $cm^{-1}$.

* * * * *